United States Patent
Fitch (10) Patent No.: US 10,393,669 B2
(45) Date of Patent: Aug. 27, 2019

(54) COLOUR MEASUREMENT OF GEMSTONES

(71) Applicant: De Beers UK Ltd, London (GB)

(72) Inventor: Alistair Fitch, Buckinghamshire (GB)

(73) Assignee: De Beers UK Ltd, London (GB)

( * ) Notice: Subject to any disclaimer, the term of this patent is extended or adjusted under 35 U.S.C. 154(b) by 0 days.

(21) Appl. No.: 15/737,196

(22) PCT Filed: Jun. 13, 2016

(86) PCT No.: PCT/GB2016/051748
§ 371 (c)(1),
(2) Date: Dec. 15, 2017

(87) PCT Pub. No.: WO2016/203210
PCT Pub. Date: Dec. 22, 2016

(65) Prior Publication Data
US 2018/0156735 A1    Jun. 7, 2018

(30) Foreign Application Priority Data
Jun. 17, 2015  (GB) .................................. 1510652.9

(51) Int. Cl.
*G01N 21/87* (2006.01)
*G01J 3/02* (2006.01)
(Continued)

(52) U.S. Cl.
CPC ............ *G01N 21/87* (2013.01); *G01J 3/0251* (2013.01); *G01J 3/462* (2013.01); *G01J 3/50* (2013.01); *G01N 21/25* (2013.01); *G01N 21/64* (2013.01)

(58) Field of Classification Search
CPC ........ G01N 21/87; G01N 21/64; G01N 21/25; G01J 3/462; G01J 3/0251; G01J 3/50
See application file for complete search history.

(56) References Cited

U.S. PATENT DOCUMENTS 4,812,903 A * 3/1989 Wagensonner ...... H04N 1/6027
  348/645
5,206,918 A * 4/1993 Levene .................... G01J 3/46
  382/110

(Continued)

FOREIGN PATENT DOCUMENTS

| WO | 96/23207 A1 | 8/1996 |
| WO | 99/61890 A1 | 12/1999 |
| WO | 02/31474 A1 | 4/2002 |

OTHER PUBLICATIONS

International Search Report and Written Opinion for corresponding International Application No. PCT/GB2016/051748 dated Oct. 4, 2016.

(Continued)

*Primary Examiner* — Mohamed K Amara
(74) *Attorney, Agent, or Firm* — Renner, Otto, Boisselle & Sklar, LLP (57) ABSTRACT

The present disclosure relates to an apparatus for measuring a color parameter of a gemstone. The apparatus comprises a support structure for supporting the gemstone at a measurement location, an illumination system for illuminating the gemstone at the measurement location, an imaging device directed towards the measurement location for obtaining an image of the gemstone, and an image processor for analyzing the image of the gemstone. The image processor is configured to identify a set of stone pixels corresponding to the gemstone in the image and identify luminance and chrominance values for each stone pixel. A color vector is calculated from an expression of the chrominance values of the stone pixels in chrominance space, the color vector extending in chrominance space from stone pixels having a relatively high luminance value to stone pixels having a relatively low luminance value. This color vector is used in the determination of the color parameter.

22 Claims, 3 Drawing Sheets

(51) Int. Cl.
*G01J 3/46* (2006.01)
*G01J 3/50* (2006.01)
*G01N 21/25* (2006.01)
*G01N 21/64* (2006.01)

(56) References Cited

U.S. PATENT DOCUMENTS

| | | | | |
|---|---|---|---|---|
| 5,563,963 | A * | 10/1996 | Kaplan | G06T 5/002 |
| | | | | 358/463 |
| 5,619,347 | A * | 4/1997 | Taniguchi | H04N 9/735 |
| | | | | 348/223.1 |
| 5,621,480 | A * | 4/1997 | Hanai | H04N 5/208 |
| | | | | 348/630 |
| 5,748,242 | A * | 5/1998 | Podilchuk | G06T 9/008 |
| | | | | 348/391.1 |
| 6,002,448 | A * | 12/1999 | Hanai | H04N 5/208 |
| | | | | 348/630 |
| 6,496,599 | B1 * | 12/2002 | Pettigrew | G01J 3/50 |
| | | | | 348/587 |
| 6,980,283 | B1 | 12/2005 | Aggarwal | |
| 7,116,831 | B2 * | 10/2006 | Mukerjee | H04N 19/117 |
| | | | | 382/236 |
| 7,702,187 | B2 * | 4/2010 | Rusman | G06F 3/014 |
| | | | | 382/321 |
| 8,317,521 | B2 * | 11/2012 | Lapa | G09B 5/02 |
| | | | | 356/30 |
| 8,705,018 | B2 * | 4/2014 | Benderly | G01N 21/87 |
| | | | | 356/30 |
| 9,128,062 | B2 * | 9/2015 | Palmieri | G01N 21/87 |
| 9,176,068 | B1 * | 11/2015 | Radomyshelsky | G01J 1/58 |
| 9,222,893 | B2 * | 12/2015 | Hornabrook | G01N 21/87 |
| 9,435,747 | B2 * | 9/2016 | Song | G01N 21/87 |
| 9,568,434 | B2 * | 2/2017 | Sim | G01N 21/87 |
| 9,953,406 | B2 * | 4/2018 | Verboven | G06T 7/0004 |
| 9,958,398 | B2 * | 5/2018 | Davies | G01N 21/87 |
| 10,006,868 | B2 * | 6/2018 | Patel | G01N 21/87 |
| 10,036,711 | B2 * | 7/2018 | Palmieri | G01N 21/01 |
| 10,054,550 | B2 * | 8/2018 | Gu | G01N 21/87 |
| 2003/0081828 | A1 * | 5/2003 | Curry | G06K 9/38 |
| | | | | 382/162 |
| 2005/0156942 | A1 * | 7/2005 | Jones | A61F 9/08 |
| | | | | 345/589 |
| 2006/0197774 | A1 * | 9/2006 | Wang | G09G 5/02 |
| | | | | 345/589 |
| 2008/0204705 | A1 | 8/2008 | Liu | |
| 2013/0201206 | A1 * | 8/2013 | Bryant | H04N 1/407 |
| | | | | 345/600 |
| 2015/0237322 | A1 * | 8/2015 | Stec | H04N 9/77 |
| | | | | 348/453 |

OTHER PUBLICATIONS

UK Search Report for corresponding UK Application No. GB1510652.9 dated Nov. 19, 2015.

* cited by examiner

COLOUR MEASUREMENT OF GEMSTONES

FIELD OF THE INVENTION

The present invention relates to colour measurement of gemstones. In particular, although not exclusively, the invention relates to the measurement of colour of diamonds.

BACKGROUND

The beauty or attractiveness of gemstones, and in particular diamonds, is considered to be directly related to how the stones interact with light. The market value of a polished diamond depends on its colour, cut proportions, internal clarity and weight, known as the "Four Cs". The cut and weight are relatively easy to measure quantitatively, but colour is generally measured by eye. In the case of colourless to light yellow coloured diamonds, an analysis is made along what is commonly referred to as the GIA D to Z scale. Typically a trained assessor visually inspects the diamond, and compares it to a set of existing sample stones of known colour. In practice, the sample stones usually have a colour which corresponds to the boundary between grades—e.g. a D/E boundary stone.

This visual inspection process is difficult, time consuming, and inevitably involves some subjective judgement. It is therefore desirable to produce an instrument which can provide a repeatable, reliable, objective quantitative measurement of the colour of a diamond. Various approaches have been tried in the past. In general, what they have in common is the illumination of the diamond by visible light, and the measurement of light transmitted from the diamond. Colour analysis of this light enables a measure of the diamond's colour to be estimated.

Although the these techniques can provide a useful indication of the colour of a diamond, in practice, simple colour analysis of the light emitted from a diamond does not always correlate exactly with colour grades issued by trained assessors. It is believed that this is due to subtle differences visible by eye which can be caused by the many different path lengths which may be followed by light transmitted by a diamond or other polished gemstone. These different path lengths are caused by internal reflection from the facets of the stone. The techniques referred to above effectively measure a single light path, a region corresponding to a collection of similar length light paths or an average of some or all light paths. A human eye, by contrast, will see an image of the whole gemstone, and can simultaneously see the colour across the stone, and variations in the apparent colour caused by differences in path length of light traversing the stone.

To be able to detect subtle variations in colour, instruments require careful calibration and a stable operating environment. This affects repeatability and reproducibility and limits the sensitivity with which colour can be measured. Furthermore, subtle variations in the hue of a diamond can have a dramatic effect on its price. For example, a diamond with a yellow hue is significantly more valuable than a similar diamond with a brown hue. Existing techniques struggle to detect these hue changes in near colourless diamonds. In addition, existing techniques measure relative to a standard or a patch of known colour. The standard or colour patch must be cleaned and maintained.

SUMMARY OF THE INVENTION

The inventors have realised that it is possible to make use the different lengths of light path within a diamond or other gemstone. Variation in colour of light transmitted along different path lengths can be identified and used to provide an indication of the colour or hue of the stone.

In accordance with one aspect of the present invention there is provided an apparatus for measuring a colour parameter of a gemstone. The apparatus comprises a support structure for supporting the gemstone at a measurement location, an illumination system for illuminating the gemstone at the measurement location, an imaging device directed towards the measurement location for obtaining an image of the gemstone, and an image processor for analysing the image of the gemstone. The image processor is configured to identify a set of stone pixels corresponding to the gemstone in the image and identify luminance and chrominance values for each stone pixel, and calculate a colour vector from an expression of the chrominance values of the stone pixels in chrominance space, the colour vector extending in chrominance space from stone pixels having a relatively high luminance value to stone pixels having a relatively low luminance value. A direction of the colour vector is used in determining the colour parameter.

The direction of the colour vector provides an indication of a hue of the stone: it provides a pointer towards the pixels representing light which has traveled along long light paths through the stone (and which therefore have relatively low luminance).

The stone pixels may be separated into a set of light pixels and an equally sized set of dark pixels, the light pixels having higher luminance values than the dark pixels, and the colour vector may then be calculated to extend from a mean chrominance of the light pixels to a mean chrominance of the dark pixels. Alternatively, the colour vector may be calculated by regression fitting of a line to the chrominance values of the stone pixels in chrominance space.

The luminance and chrominance values may be defined in the CIE L*a*b* colour space.

Stone pixels may be excluded from analysis on the basis of predetermined thresholds so that exceptionally bright and exceptionally dark pixels within the boundaries of the gemstone are excluded from the set of stone pixels and do not contribute towards the determination of the colour vector.

The apparatus may further comprise a rotation device may be for rotating the support structure. Images of the gemstone may be obtained at a plurality of different rotational positions, and a colour vector determined from each image. These colour vectors may be combined to generate a combined colour vector for the gemstone for use in determining the colour parameter of the gemstone.

The combined colour vector for the gemstone may be calculated by adding or averaging colour vectors from images at the different rotational positions. Alternatively, the combined colour vector for the gemstone may be calculated from an expression in chrominance space of the chrominance values of the stone pixels from all of the images: the combined colour vector extends in chrominance space from pixels having a relatively high luminance value to pixels having a relatively low luminance value.

A mean luminance and/or chrominance of the stone pixels may be calculated and used to determine a further colour parameter. It may be that this further colour parameter provides a general colour for the stone, and the parameter calculated from the colour vector provides a more subtle indication of its hue.

The gemstone may be a diamond, and the colour parameter included in a determination of a colour grade and/or subgrade of the diamond.

The illumination system may include a visible light source and a diffusion mechanism for ensuring that the gemstone is illuminated by diffuse visible light.

The apparatus may further include an ultra-violet light source. At least one fluorescence image of the gemstone may be obtained when illuminated by ultra-violet light, and a measure of fluorescence of the gemstone may be provided from an analysis of said fluorescence image.

The image detector may be configured to obtain a visible image of the gemstone when illuminated by visible light and a fluorescence image of the gemstone at the same position when illuminated by ultra-violet light, the stone pixels may then be identified from the visible image, and only the corresponding stone pixels in the fluorescence image included in the analysis.

In accordance with another aspect of the present invention there is provided a method of measuring a colour parameter of a gemstone. The method comprises illuminating the gemstone with visible light and obtaining an image of the gemstone when so illuminated. The method further comprises identifying a set of stone pixels, corresponding to the gemstone, in the image, and identifying luminance and chrominance values for each stone pixel. A colour vector is calculated from an expression of the chrominance values of the stone pixels in chrominance space, the colour vector extending in chrominance space from stone pixels having a relatively high luminance value to stone pixels having a relatively low luminance value. A direction of the colour vector is used in determining the colour parameter.

BRIEF DESCRIPTION OF THE DRAWINGS

Some preferred embodiments of the invention will now be described by way of example only and with reference to the accompanying drawings, in which.

DETAILED DESCRIPTION OF THE INVENTION

Figure 1:
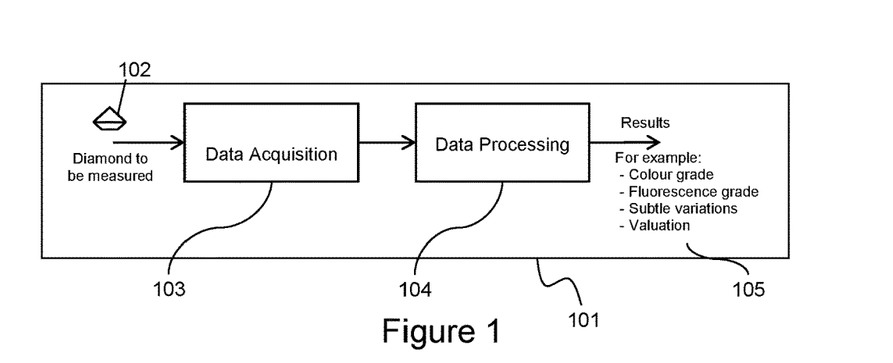
FIG. 1 is a functional illustration of a system for automatically assigning a colour grade to a diamond.

FIG. 1 is a functional illustration of a system 101 suitable for measuring the colour and/or fluorescence of an object such as a gemstone 102. It has particular application to the measurement of colour and fluorescence of a polished gemstone such as a polished diamond, but it will be appreciated that the same techniques can in some circumstances be used to obtain useful data about rough stones. For simplicity, the following discussion will concentrate on the measurement of colour and fluorescence in polished diamonds, but it will be understood that this is by way of example only.

The apparatus is intended to provide an output of colour and/or fluorescence information about the diamond. For example this could be the colour grade, fluorescence grade, hue, shade or other information which affects the value of the diamond.

In essence, the system 101 allows for the introduction of diamond 102 or other gemstone. The system includes a data acquisition module 103 and data processing module 104. Results 105 are output from the data processing module 104. The results may include a colour grade and/or subgrade for the diamond, a fluorescence grade, further quantitative measures related to subtle variations of colour, and further information relevant to valuation of the stone. At least some of such results may be seen as colour parameters of the stone.

Figure 2:
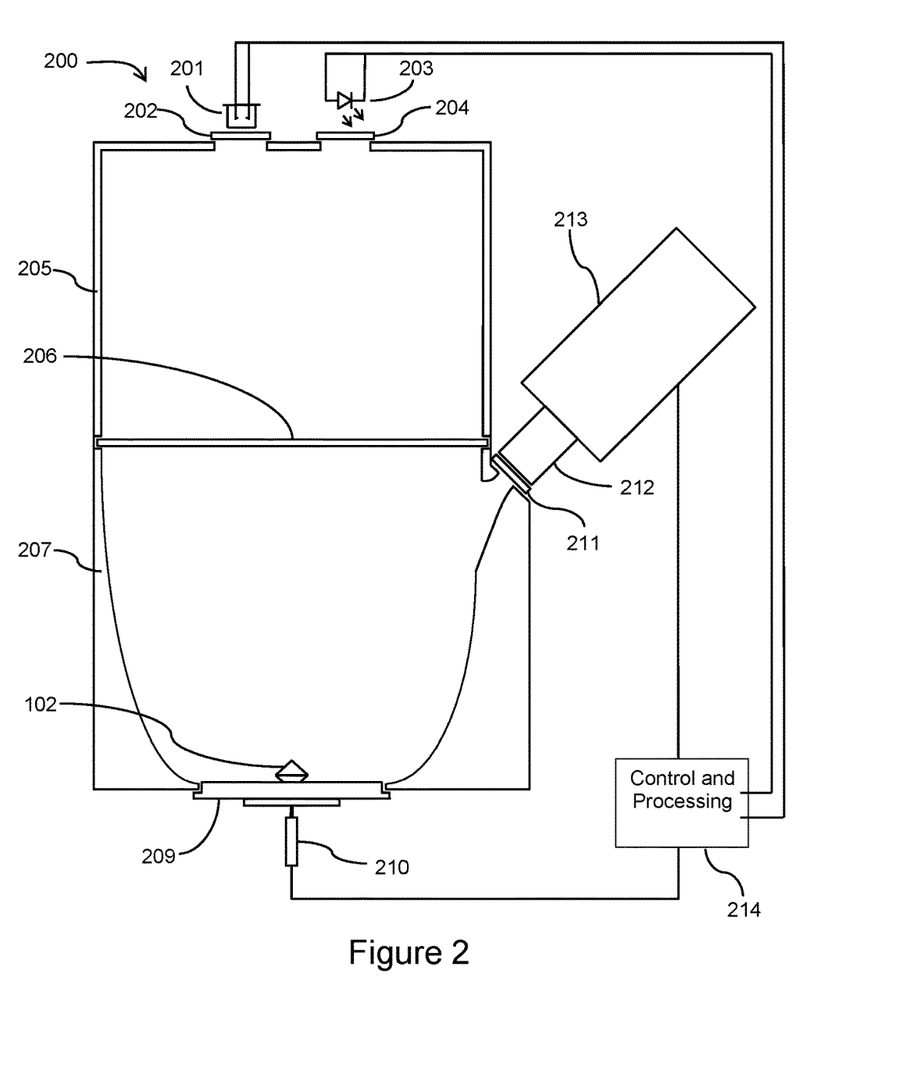
FIG. 2 is a schematic illustration of an apparatus suitable for use in acquiring data from a diamond and processing the data to output a colour and fluorescence measurement and/or grade.

FIG. 2 is a schematic illustration of an instrument 200 suitable for use as the data acquisition and data processing modules 103, 104 shown in FIG. 1. The instrument includes a visible light source 201 to provide visible light used for colour measurement. In this example the light source 201 is a xenon strobe with a long-pass filter 202 to remove ultra-violet light. The strobe could be an Excelitas PAX-10 and the filter 202 could be a colourless UV-absorbing long-pass filter with a cut at 395 nm. Alternative light sources such as light emitting diodes (LEDs) or halogen bulbs could be used. One or multiple light sources could be used.

An ultra-violet light source 203 provides light used for fluorescence measurement. For example this may comprise an LED array with a filter 204 to remove visible wavelengths of light. An example ultra-violet source is the ENFIS UNO Tag Array Ultra-Violet 375 nm LED. An example filter is the Edmund optics 400 nm, 12.5 mm diameter OD2 short-pass filter.

The visible and uv light sources 202, 204 emit light into a diffusion chamber so as to obtain diffuse light. Various suitable arrangements may be envisaged, but one exemplary arrangement includes a cylinder 205 coated with Barium Sulphate and closed by a sheet of diffuse glass 206. In one example the cylinder may have a diameter of about 100 mm. The diffusion chamber 205 sits above a measurement chamber 207, separated therefrom by the diffuse glass sheet 206, so that diffuse visible and/or uv light is emitted from the diffusion chamber 205 into the measurement chamber 207.

The exemplary measurement chamber arrangement 207 shown in FIG. 2 includes a modified hemisphere coated in Barium Sulphate. The top of the measurement 207 chamber is circular with a diameter of 100 mm. The bottom of the measurement chamber is a hemisphere with a 50 mm hole at the bottom. The hole allows the top of a platform 209 to enter and exit the measurement chamber.

The platform 209 is intended to support the diamond 102. The platform is rotatable and coupled to a motor 210. The platform may be made from virgin PTFE, and is preferably opaque.

The measurement chamber includes an exit hole through which light emitted by or passing through the diamond can leave the chamber. Behind the exit hole is a filter 211, lens 212 and camera 213 or other imaging device. The filter 211 is designed to select required wavelengths of light for observation, and preferably blocks ultra-violet light. An example is the Comar 405 IY long-pass dichroic filter.

The lens 212 focuses light from the measurement chamber 207 onto the image plane of the camera 213. In this example the lens 212 observes the platform 209 at approximately 49 degrees to the normal of the platform. An example lens is the Schneider Xenoplan 1.4/17.

The camera 213 converts light into electronic signals. Combined with the above the camera produces an image of the diamond 102 under controlled conditions. In the preferred embodiment the camera is a JAI M9. The JAI M9 is a 3CCD camera with three ⅓" progressive scan CCDs and 1024×768 active pixels.

A control and processing unit 214, for example a microcontroller and a PC, is configured to control the loading mechanism (not shown), visible illumination, ultra-violet illumination, rotation of platform and triggering of the camera. The processing unit also receives images obtained by the camera 213 and performs analysis. The processing unit is described in further detail below.

In use, rotation of the platform 209 is synchronised with the camera 213 and lighting 201, 203. This is achieved by rotating the platform at a set speed and a set time between each image capture. In one example the platform is rotated at 1.548 revolutions per second, and images captured at 34 ms intervals.

A loading mechanism (not shown in FIG. 2) is used to introduce the diamond 102 into the measurement chamber 207. To load the diamond 102, the platform 209 is held below and in front of the measurement cell 207 by a tray. The diamond is placed on the tray. During loading the tray first carries the platform to a location under the measurement cell. Then the motor 210 and platform 209 are lifted simultaneously so as to lift the platform 209 into the measurement cell. The process is reversed for unloading.

In order to acquire data, the diamond 102 is placed table down on the platform 209. The loading mechanism brings the platform 209 into the measurement cell 207. For colour measurement the visible light source 201 is used. For fluorescence measurement the ultra-violet source 203 is used. In each case the measurement cell is flooded with diffuse light from the chosen source and an image is obtained by the camera 213. The platform 209 is rotated and another image taken. This is repeated until sufficient images have been captured. Typically 18 images are captured. The lighting conditions are consistent for the visible images. The images are transferred to the processing unit 214.

The illumination, optics and camera are controlled for optimal utilisation of the camera's dynamic range. This is set during commissioning and changed only if required, optionally after about a month. The camera 213 is controlled and tested to maintain consistent imaging conditions. This is automatically tested on a daily basis. The camera is controlled and tested to provide a known light response. As is usual, the camera captures three intensity ("greyscale") images of different parts of the electromagnetic spectrum. These greyscale images can be combined to form a colour image.

The temperature of the camera is measured. This is used to ensure calibration and measurement images are taken under similar temperatures. Similar temperatures are typically within 5 degrees Celsius.

Colour or fluorescence is measured from the images. Measurement is calibrated to a global standard. Colour measurement is translated to a colour grade and sub-grade. Fluorescence measurement is translated to a fluorescence grade and sub-grade. Sub-grades indicated the position within a grade.

Three sets of data are produced:
1. Image assessment and calibration data
2. Stone measurement data
3. Stone calibration data.

The processing of each of these sets of data is described below.

Image Assessment and Calibration

Image assessment and calibration data consists of:
a) A plurality (e.g. 11) of pairs of images captured at differing light levels. These images are used to assess the camera response. The camera's light response is measured and tested to be appropriate for subsequent colour space conversion.
b) A plurality (e.g. 18) of visible light images of the platform without a stone. Where eighteen images are obtained, the platform is rotated by 360/19 degrees between each image. These images are used to assess the cleanliness of the platform. These images are used with the dark images (described below) for image calibration.
c) A plurality (e.g. 18) of "dark" images of the platform without a stone. These images are captured without visible or fluorescence illumination. These are used with the 18 light images for image calibration.

In the preferred embodiment the camera has a linear response allowing a linear model for image calibration. If a non-linear response is found the appropriate non-linear model would be used for image calibration.

Image calibration accounts for spatial non-uniformity across the image. The cause of the non-uniformity can be the measurement cell, the optics or the camera. After image calibration measurement should be invariant to spatial position in the image.

There are multiple approaches to implementing image calibration. In a preferred embodiment the 18 light images are combined into a single low noise light image. The 18 dark images are combined into a low noise dark image. Low noise images can be achieved with alternative means such as a single image and a smoothing operation. From the low noise light and dark images a linear mapping is calculated for each image picture element (pixel). Alternatively the spatial changes can be described with an appropriate function and a single mapping can be calculated.

Stone Measurement

Figure 3:
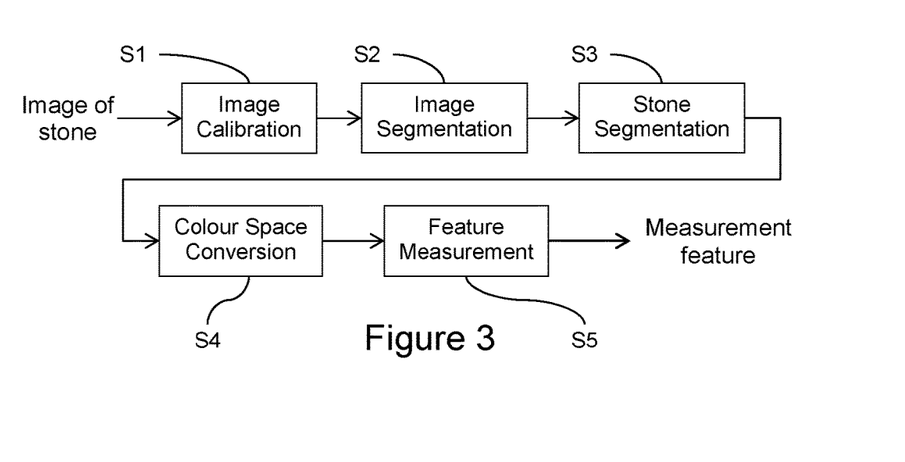
FIG. 3 is a flow diagram showing the steps involved in processing data obtained using the apparatus of FIG. 2.

In a preferred embodiment colour is measured from a number of separate images of the stone 102, at different rotational positions, illuminated by visible light. In one example 18 visible images of the stone are obtained, in which case the platform may be rotated by 360/19 degrees between each image. FIG. 3 is an illustrative flow diagram showing how each image is processed to produce a "measurement feature" which is a feature providing an indication, from that image, of a colour parameter of the stone. The measurement features or colour parameters from each individual image may be combined to give a corresponding colour parameter for the whole stone. A colour grade for the stone may be determined on the basis of one or more of these colour parameters.

In more detail, with reference to FIG. 3, each image is processed as follows:

Image Calibration (S1): The purpose of image calibration is to account for spatial variation across the image. For example dark and visible light images of the empty platform can be used to calculate coefficients of an equation to transform each channel (RGB) of each picture element (pixel) to give an equal response. For example this could be a first order equation with gain and offset. In this case applying the Image Calibration involves multiplying each channel of each pixel by its gain and adding the corresponding offset.

Image Segmentation (S2): The image is segmented to identify the pixels corresponding to the stone in the image ("stone pixels"). For example this can be achieved by selecting only pixels below a predetermined threshold for at least one out of RGB value. Part of the non-stone region can be used as a colour reference. This reference patch is also identified during image segmentation.

Stone Segmentation (S3): Stone segmentation involves further analysis of the set of stone pixels so as to identify pixels which are not of interest and remove them so they are not included in later analysis. For example, stone segmentation can identify pixels of interest by assessing their R/G/B intensity (greyscale) values. For example pixels in highlights are brighter than other elements in the scene so can be identified and excluded. Similarly, pixels covering piques are unusually dark so can be identified and excluded.

Colour Space Conversion (S4): The colour image is converted from an additive colour model to a colour space with separate luminance and chrominance. For example each picture element can be converted from Red, Green and Blue (RGB) to CIE L*a*b*. In this case the luminance information is present in the L* channel and the chrominance information in the a* and b* channels.

Feature Measurement (S5): The colour pixels are processed to produce one or more measurement features or colour parameters, each of which is a potential indicator of colour. A colour parameter may include statistical measures and/or a colour vector (described in more detail below). Example statistical measures include the mean of L*, a* and b* over all the stone pixels (except those pixels excluded in step S3). In this case the mean L* value indicates how light or dark the diamond is, a negative a* indicates a green colour, positive a* a red colour, negative b* a blue colour and positive b* a yellow colour.

The statistical measurements described above can give a broad indication of the colour of the stone, even from one image, using the L, a* and b* means. However, as previously discussed, the colour perceived by a user can be affected by more subtle changes caused by variations in colour across individual images, and in particular by colour being emphasised where in regions where light follows a long path length through the stone.

These subtle variations can be quantified by calculating a colour vector which may form the basis of a colour parameter. The magnitude and angle of the colour vector describe subtle colour variations within the diamond. The following discussion explains how the colour vector is determined.

The luminance and chrominance of each stone pixel in each image is determined by the light exiting the stone at that point and being detected by the camera. This light is effectively a summation of a set of light paths. For the purpose of this description each stone pixel can be considered to be a result of a corresponding light path. Some of the stone pixels have corresponding light paths which are relatively short, have a low level of absorption and show the colour of the diamond only weakly. Other stone pixels have corresponding light paths which are relatively long, have a high level of absorption and strongly show the colour of the diamond. Taken as a whole the stone pixels have a range of corresponding light paths with a range of absorptions and a range of strengths of colour. The length of light path is proportional to the strength of colour. It should also be appreciated that shorter paths have lower absorption and therefore generally lead to lighter pixels.

The Colour Vector can be calculated as follows. The colour of each stone pixel is expressed in a chromaticity space such as CIE L*a*b*. The stone pixels can be split into "light" stone pixels and "dark" stone pixels on the basis of their luminance value. The light stone pixels correspond to short light paths. The dark stone pixels correspond to longer light paths. Colour measures for each sub-set of stone pixels are combined to give colour measures for light and dark stone pixels. Colour measures of light and dark stone pixels are the respective start and end points of the colour vector. From the colour vector a magnitude and direction (angle) are calculated.

Figure 4A:
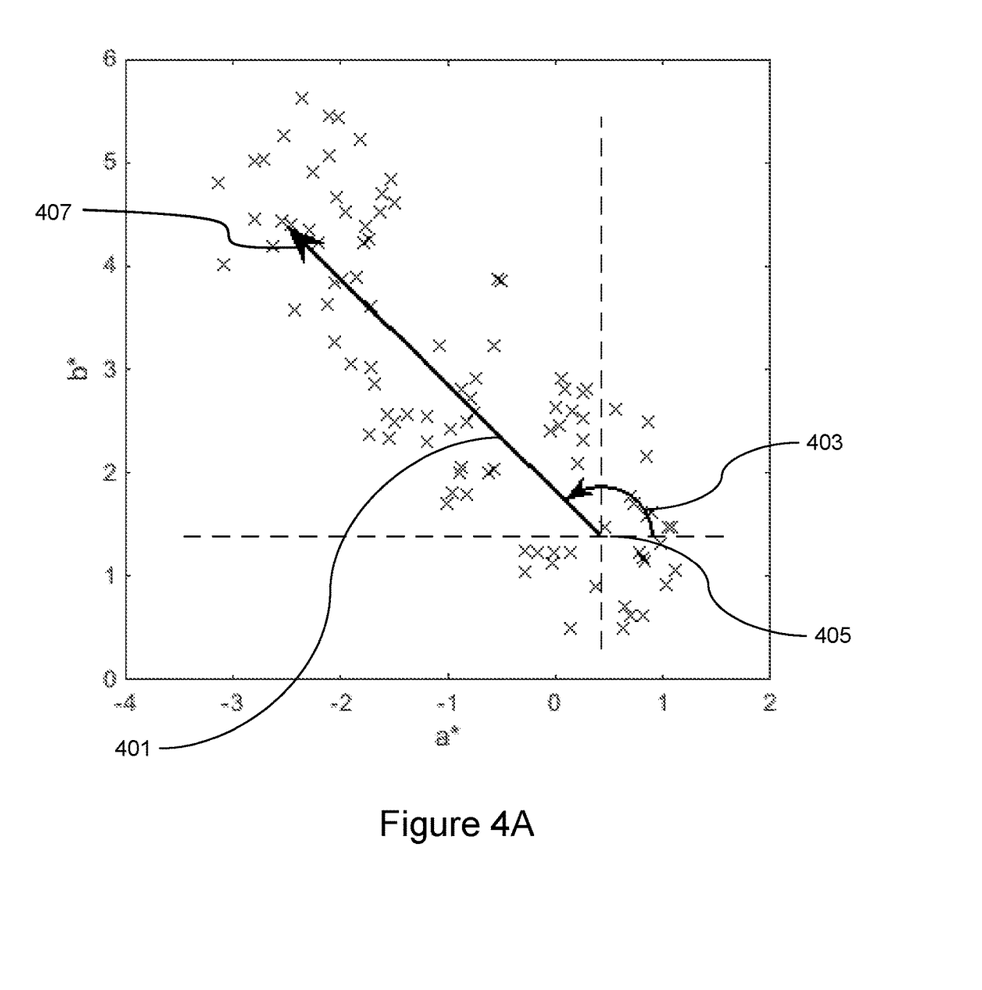
FIGS. 4A and 4B are graphs illustrating colour vectors indicating hue of a diamond.
Figure 4B:
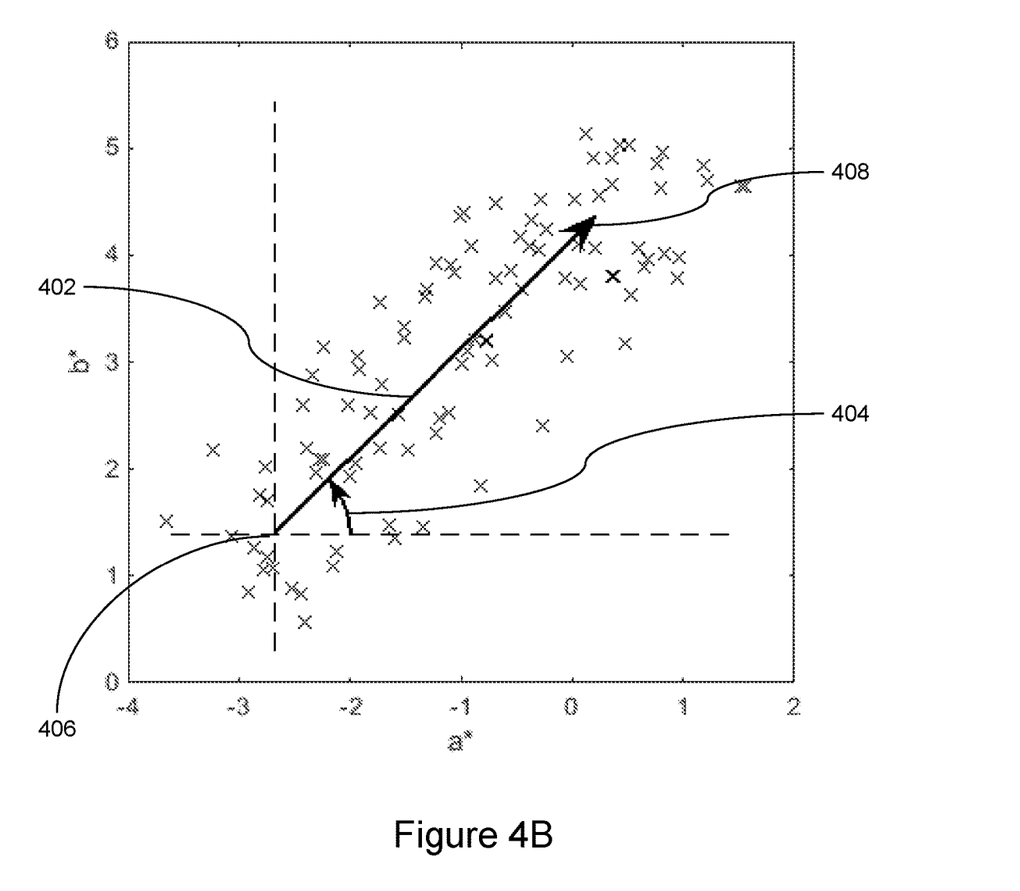

This approach can be understood with reference to FIGS. 4A and 4B, each of which shows graphs of CIE a*b* values of all of the stone pixels of a single image (100 pixels in each case), taken from different stones. The average colour (mean a*, b*) of the pixels in each graph is the same (mean a*=−1, mean b*=3), but the distribution is different. The colour vector 401, 402 is a way of quantifying this distribution by assigning an angle 403, 404 and a magnitude.

The angle 403, 404 corresponds to the direction of the distribution. The angle effectively indicates the hue expected of light travelling along a very long light path in the diamond. The magnitude corresponds to the spread of the distribution. The magnitude indicates the strength of the colour in that particular image.

For example, in a simple process the colour vector can be calculated by partitioning the pixels by L* into a light half and a dark half. The mean a* and b* values of each of the light and dark sets of pixels are calculated. The start of each vector 405, 406 is the average a*, b* of the light pixels in that image. The end 407, 408 of the vector is the mean a*, b* of the dark pixels of that image.

More sophisticated fitting algorithms may also be envisaged, and stone pixels can be processed in alternative ways to produce a colour vector. For example regression can be applied to fit a line in the colour space. Points can be projected onto the line and interquartile ranges used to define the start and end of the colour vector. Vector direction could be determined by assessing L* values or proximity to the origin. Alternatively, rather than simply splitting the pixels on the basis of luminance into "light" and "dark", they could be split into three or more sets (e.g. light, medium and dark) and a line used to fit the mean values from each of these sets.

It will be apparent that the colour vector can provide significant additional information not apparent from the mean chrominance of the stone pixels in an image. In the example of FIG. 4A, an angle of about 130° indicates negative a* and positive b*, and thus a green-yellow colour, which would be in line with the mean a*,b* (−1,3) of all of the pixels. In FIG. 4B, where the mean a*,b* is again (−1,3), the colour vector has an angle of about 45°, indicating a red-yellow (or orange) colour. This could manifest itself as a generally yellow diamond appearing brown to the viewer, but would not be apparent from the simple colour averaging of all of the pixels.

At very low magnitudes the angle can be an unreliable indicator of hue. The magnitude of the colour vector can therefore be used as a filter to determine the confidence with which the angle can be interpreted. In addition, the magnitude of the colour vector does a reasonable job of grading colour.

As discussed above, colour can be measured from a single image. To increase robustness and accuracy many images of a single diamond may be obtained and the measurements combined. Usually the diamond is rotated between the images. Fusion techniques are used to combine the measurement features of each image into a measurement feature (colour parameter) for the diamond. For example the median operator can be used to combine the mean L* features of each image to give a single mean L* for the whole stone. Alternatively the features can be combined with a maximum operation. Alternatively the features can be combined with a mean operation.

FIGS. 4A and 4B show colour vectors for individual images (from different stones). In order to combine the colour vectors for all of the images taken of a particular stone, a number of techniques may be used. Each vector can be simply expressed in Cartesian coordinates as (a*,b*) so one way of combining the vectors is simply to take the mean values from all of the images, although in practice it has been found that a median is more useful, because in some circumstances one or two images may result in outliers (for example if one or more image is corrupt). Another alternative is to include all the stone pixels from all of the images in a single graph and calculate a single colour vector from the complete dataset.

Fluorescence can be measured with one visible light image and one ultra-violet light image. The platform is not rotated between the images. The visible light image is used to locate the stone pixels. The corresponding pixels in the ultra-violet light image are used to measure the fluorescence. An indication of the fluorescence of the stone (a "fluorescence feature") is measured from the stone pixels. This may be, for example, the mean, mode or median colour value of all of the stone pixels when illuminated by uv light.

It is of course possible to rotate the stone and obtain different fluorescence features at each rotational position—and potentially even carry out an analysis so as to obtain a colour vector for fluorescence—but in general detection of subtle colour change in fluorescence is not normally required.

Repeatability is maintained through the use of a colour sample. Each stone in a colour sample is individually measured. These measures are compared to the expected result. The colour response of the software can be adjusted to compensate if the sample is not as expected, and this operates as a feedback loop. Typically the system is tested daily. Typically the system is Stone Calibrated once a month. Stone calibration is applied to measurement features to ensure repeatable measures between different machines, different locations and at different times.

Colour parameters are used to classify a diamond to a colour grade. The fluorescence feature is used to assign a fluorescence grade. For both colour and fluorescence a subgrade is used to indicate a diamonds position within a grade.

For example the colour parameter CIE b* can be used to assign a colour grade based on the intensity of yellow. The boundaries used to assign grades are determined by measuring 1000's of diamonds of known colour grades. CIE L* feature can be used to determine if the diamond is grey. The colour vector can be used to determine if the diamond has a non-yellow hue. As previously mentioned, the magnitude of the colour vector may also be used to assist assigning a colour grade.

In a preferred embodiment the fluorescence feature is processed to obtain a single measure of fluorescence intensity. 1000's of fluorescence stones have been measured to calculate fluorescence boundaries. These boundaries determine the fluorescence grade.

The invention claimed is:

1. Apparatus for measuring a colour parameter of a gemstone, comprising:
    a support structure for supporting the gemstone at a measurement location;
    an illumination source for illuminating the gemstone at the measurement location;
    an imaging device directed towards the measurement location for obtaining an image of the gemstone; and
    an image processor for analysing the image of the gemstone, the image processor configured to:
        identify a set of stone pixels corresponding to the gemstone in the image;
        identify luminance and chrominance values for each stone pixel;
        calculate a colour vector from an expression of the chrominance values of the stone pixels in chrominance space, the colour vector extending in chrominance space from stone pixels having a relatively high luminance value to stone pixels having a relatively low luminance value; and
        determining the colour parameter using the direction of the colour vector that extends from the stone pixels having the relatively high luminance value to the stone pixels having the relatively low luminance value in the chrominance space.

2. The apparatus of claim 1, wherein the image processor is configured to separate the stone pixels into a set of light pixels and an equally sized set of dark pixels, the light pixels having higher luminance values than the dark pixels, and to calculate the colour vector to extend from a mean chrominance of the light pixels to a mean chrominance of the dark pixels.

3. The apparatus of claim 1, wherein the colour vector is calculated by regression fitting of a line to the chrominance values of the stone pixels in chrominance space.

4. The apparatus of claim 1, wherein the image processor is configured to define the luminance and chrominance values of the stone pixels in the CIE L*a*b* colour space.

5. The apparatus of claim 1, wherein the image processor is configured to exclude stone pixels from analysis on the basis of predetermined thresholds so that pixels within the boundaries of the gemstone having a brightness above a predetermined brightness threshold or below a predetermined darkness threshold are excluded from the set of stone pixels and do not contribute towards the determination of the colour vector.

6. The apparatus of claim 1, further comprising a rotation device for rotating the support structure, wherein:
    the imaging device is configured to obtain images of the gemstone at a plurality of different rotational positions; and
    the image processor is configured to determine a colour vector from each image and combine the colour vectors to generate a combined colour vector for the gemstone for use in determining the colour parameter of the gemstone.

7. The apparatus of claim 6, wherein the image processor is configured to calculate the combined colour vector for the gemstone by adding or averaging colour vectors from images at the different rotational positions.

8. The apparatus of claim 6, wherein the image processor is configured to calculate the combined colour vector for the gemstone from an expression in chrominance space of the chrominance values of the stone pixels from all of the images, the combined colour vector extending in chrominance space from pixels having a relatively high luminance value to pixels having a relatively low luminance value.

9. The apparatus of claim 1, wherein the image processor is configured to calculate a mean luminance and/or chrominance of the stone pixels, and to determine a further colour parameter from the calculated mean luminance and/or chrominance.

10. The apparatus of claim 1, wherein the gemstone is a diamond and the image processor is configured to include the colour parameter in a determination of a colour grade and/or subgrade of the diamond.

11. The apparatus of claim 1, wherein the illumination source includes a visible light source and a diffusion mechanism for ensuring that the gemstone is illuminated by diffuse visible light.

12. The apparatus of claim 11, further including an ultra-violet light source, wherein the imaging device is configured to obtain at least one fluorescence image of the gemstone when illuminated by ultra-violet light, and the image processor is configured to provide a measure of fluorescence of the gemstone from an analysis of said fluorescence image.

13. The apparatus of claim 12, wherein the image detector is configured to obtain a visible image of the gemstone when illuminated by visible light and a fluorescence image of the gemstone at the same position when illuminated by ultra-violet light, and wherein the image processor is configured to identify the stone pixels from the visible image and include only the corresponding stone pixels in the fluorescence image in the analysis.

14. A method of measuring a colour parameter of a gemstone, comprising:
    illuminating the gemstone with visible light;
    obtaining an image of the gemstone when illuminated;
    identifying a set of stone pixels, corresponding to the gemstone, in the image;
    identifying luminance and chrominance values for each stone pixel;
    calculating a colour vector from an expression of the chrominance values of the stone pixels in chrominance space, the colour vector extending in chrominance space from stone pixels having a relatively high luminance value to stone pixels having a relatively low luminance value; and
    determining the colour parameter using the direction of the colour vector that extends from the stone pixels having the relatively high luminance value to the stone pixels having the relatively low luminance value in the chrominance space.

15. The method of claim 14, further comprising separating the stone pixels into a set of light pixels and an equally sized set of dark pixels, the light pixels having higher luminance values than the dark pixels, and calculating the colour vector to extend from a mean chrominance of the light pixels to a mean chrominance of the dark pixels.

16. The method of claim 14, further comprising calculating the colour vector by regression fitting of a line to the chrominance values of the object pixels in chrominance space.

17. The method of claim 14, further comprising excluding stone pixels from analysis on the basis of predetermined thresholds so that pixels within the boundaries of the gemstone having a brightness above a predetermined brightness threshold or below a predetermined darkness threshold are excluded from the set of stone pixels and do not contribute towards the determination of the colour vector.

18. The method of claim 14, further comprising:
    obtaining images of the gemstone at a plurality of different rotational positions;
    determining a colour vector from each image;
    combining the colour vectors to generate a combined colour vector for the gemstone; and
    determining the colour parameter of the gemstone using the combined colour vector.

19. The method of claim 18, wherein the colour vectors are combined by adding or averaging colour vectors from images at the different rotational positions.

20. The method of claim 18, wherein the colour vectors are combined by expressing in chrominance space the chrominance values of the stone pixels from all of the images, the combined colour vector extending in chrominance space from pixels having a relatively high luminance value to pixels having a relatively low luminance value.

21. The method of claim 14, wherein the gemstone is a diamond and the method further comprises determining a colour grade and/or subgrade of the diamond using the colour parameter.

22. The method of claim 14, further comprising:
    illuminating the gemstone with ultra-violet light;
    obtaining a fluorescence image of the gemstone when so illuminated; and
    determining a measure of fluorescence of the gemstone from an analysis of said fluorescence image.

\* \* \* \* \*